United States Patent
Umemoto et al.

(10) Patent No.: US 12,036,315 B2
(45) Date of Patent: Jul. 16, 2024

(54) PHARMACEUTICAL COMPOSITION FOR ORAL ADMINISTRATION COMPRISING ENZALUTAMIDE

(71) Applicant: Astellas Pharma Inc., Tokyo (JP)

(72) Inventors: Yoshiaki Umemoto, Tokyo (JP); Takatsune Yoshida, Tokyo (JP); Sachie Namiki, Tokyo (JP); Akira Takagi, Tokyo (JP); Ryo Kojima, Tokyo (JP); Toshiro Sakai, Tokyo (JP); Shinsuke Oba, Tokyo (JP); Hajime Aoki, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 16/609,062

(22) PCT Filed: Apr. 27, 2018

(86) PCT No.: PCT/JP2018/017159
§ 371 (c)(1),
(2) Date: Oct. 28, 2019

(87) PCT Pub. No.: WO2018/199282
PCT Pub. Date: Nov. 1, 2018

(65) Prior Publication Data
US 2020/0146977 A1 May 14, 2020

(30) Foreign Application Priority Data
Apr. 28, 2017 (JP) .................. 2017-090300

(51) Int. Cl.
*A61K 9/20* (2006.01)
*A61K 9/00* (2006.01)
(Continued)

(52) U.S. Cl.
CPC .......... *A61K 9/0053* (2013.01); *A61K 9/2009* (2013.01); *A61K 9/2027* (2013.01); *A61K 9/2054* (2013.01); *A61K 31/4166* (2013.01)

(58) Field of Classification Search
CPC .... A61K 9/1635; A61K 9/2027; A61K 9/284; A61K 31/4166
See application file for complete search history.

(56) References Cited

U.S. PATENT DOCUMENTS 6,156,343 A 12/2000 Morita et al.
10,406,107 B2 * 9/2019 Maruyama ........... A61K 31/167
(Continued)

FOREIGN PATENT DOCUMENTS

EP 2335697 A1 6/2011
JP H10316576 A 12/1998
(Continued)

OTHER PUBLICATIONS

Brough et al., Use of Polyvinyl Alcohol as a Solubility-Enhancing Polymer for Poorly Water Soluble Drug Delivery (Part 1), AAPS PharmSciTech 17, 167-179, 2015.
(Continued)

*Primary Examiner* — Lakshmi S Channavajjala
(74) *Attorney, Agent, or Firm* — Banner & Witcoff, Ltd.

(57) ABSTRACT

Provided is a pharmaceutical composition for oral administration in which the solubility and/or dissolution properties of enzalutamide are improved and supersaturation is maintained. Also provided is a pharmaceutical composition for oral administration in which the oral absorbability of enzalutamide is improved. The pharmaceutical composition for oral administration comprises enzalutamide and polyvinyl alcohol.

17 Claims, 1 Drawing Sheet

(51) Int. Cl.
*A61K 9/16* (2006.01)
*A61K 31/4166* (2006.01)

(56) References Cited

U.S. PATENT DOCUMENTS

| 2014/0179749 | A1 | 6/2014 | Lorenz et al. | |
|---|---|---|---|---|
| 2014/0212461 | A1 | 7/2014 | Lickrish et al. | |
| 2016/0346198 | A1* | 12/2016 | Marota | A61K 9/2059 |
| 2016/0346207 | A1* | 12/2016 | Grahek | A61K 9/485 |
| 2017/0035773 | A1 | 2/2017 | Tomimatsu et al. | |
| 2020/0060976 | A1* | 2/2020 | Lorenz | A61K 9/16 |

FOREIGN PATENT DOCUMENTS

| JP | 2014-508812 A | 4/2014 |
|---|---|---|
| JP | 2015054471 A | 3/2015 |
| JP | 2015-527411 A | 9/2015 |
| JP | 2016056208 A | 4/2016 |
| JP | 2016172708 A | 9/2016 |
| JP | 2017-507928 A | 3/2017 |
| KR | 10-2016-0113294 A | 9/2016 |
| RU | 2205191 C1 | 5/2003 |
| WO | 2006124118 A1 | 11/2006 |
| WO | 2007127010 A2 | 11/2007 |
| WO | 2014043208 A1 | 3/2014 |
| WO | 2014167428 A2 | 10/2014 |
| WO | 2015115453 A1 | 8/2015 |
| WO | 2015118015 A1 | 8/2015 |
| WO | 2015163448 A1 | 10/2015 |
| WO | 2016116121 A1 | 7/2016 |

OTHER PUBLICATIONS

Brough et al., Use of Polyvinyl Alcohol as a Solubility-Enhancing Polymer for Poorly Water Soluble Drug Delivery (Part 2), AAPS PharmSciTech 17, 180-190, 2016.
Kestur et al., "Influence of polymer chemistry on crystal growth inhibition of two chemically diverse organic molecules," CrystEngComm 13, 6712-18, 2011.
EP 18791486.6 Extended European Search Report, dated Dec. 21, 2020.
PCTJP2018017159 International Preliminary Report on Patentability, dated Oct. 29, 2019.
PCTJP2018017159 International Search Report, dated Jul. 3, 2018.
"Handbook of Pharmaceutical Excipients", Fifth Edition, Edited by Raymond C. Rowe, Pharmaceutical Press and American Pharmacists Association 2006, pp. 592-593, 600, 694, 671.
DeJaeghere, Wesley, "Partially Hydrolyzed Polyvinyl Alcohol as Functional Excipient in Oral Solid Dosage Forms Prepared via Extrusion", 2016, 175 pages.
Markl & Zeitler, "A Review of Disintegration Mechanisms and Measurement Techniques," Pharm. Res. 34, 890-917, 2017.
Kawakami, "Pharmaceutical Technology Using Amorphous State", Pharmacia, 2016, vol. 52, No. 5, p. 402-406.
Huang, "New Dosage Form and New Technology of Modern Practical Chinese Medicine," People's Medical Publishing House, 1st edition, published on Apr. 30, 2001, p. 113.
Noh et al., "Synthesis and Application of PVA Resins With Various Molecular Variables," Polymer Science and Technology 15(1), 2004, 17 pages including translation.

* cited by examiner

PHARMACEUTICAL COMPOSITION FOR ORAL ADMINISTRATION COMPRISING ENZALUTAMIDE

TECHNICAL FIELD

The present invention relates to a pharmaceutical composition for oral administration, in which the oral absorbability of enzalutamide is improved.

More particularly, the present invention relates to a pharmaceutical composition for oral administration comprising enzalutamide and polyvinyl alcohol.

BACKGROUND ART

In recent drug discovery research, poorly water-soluble drugs often become candidates for development. Alternatively, there is also a need to improve medical opportunities through early provision of therapeutic drugs in clinical settings, and general-purpose solubilization technology remains an important issue.

Enzalutamide is an androgen receptor signaling inhibitor. The chemical name is 4-{3-[4-cyano-3-(trifluoromethyl)phenyl]-5,5-dimethyl-4-oxo-2-sulfanylideneimidazolidin-1-yl}-2-fluoro-N-methylbenzamide, and is represented by the following chemical structural formula:

[Chem. 1]

Enzalutamide is known as an active ingredient in therapeutic agents for metastatic castration-resistant prostate cancer or the like (Patent literature 1). Enzalutamide is on the market as soft capsules ("XTANDI (registered trademark)") comprising 40 mg of enzalutamide per capsule and pharmaceutical additives. According to the Package Insert of the product (Non-patent literature 1), 160 mg is orally administered to an adult once daily, and this indicates that capsules with a major axis of approximately 21 mm and a minor axis of approximately 10 mm are taken in one dose of four capsules. In particular, a reasonably sized single tablet containing a predetermined amount of enzalutamide and having appropriate and good solubility and/or dissolution stability, and oral absorbability, would be useful as a suitable replacement for the soft capsules.

As methods of solubilizing enzalutamide, a method of amorphizing enzalutamide, and a method of preparing a solid dispersion of enzalutamide with a carrier, are known (Patent literatures 2 to 4).

CITATION LIST

Patent Literature

[Patent literature 1] WO 2006/124118
[Patent literature 2] WO 2014/043208
[Patent literature 3] WO 2014/041487
[Patent literature 4] WO 2014/167428

Non-Patent Literature

[Non-patent literature 1] "XTANDI (registered trademark) Capsule 40 mg" Package Insert

SUMMARY OF INVENTION

Technical Problem

Even in the current situation, formulation design to improve the solubility of enzalutamide and improve the oral absorbability in a pH-independent manner is an important technical problem for the efficacy expression of the drug, and there is room for further improvement.

An object of the present invention is to provide a pharmaceutical composition for oral administration in which, in a pH-independent manner, the solubility and/or the dissolution properties of enzalutamide are improved, and supersaturation is maintained. Another object of the present invention is to provide a pharmaceutical composition for oral administration in which the oral absorbability is improved.

Solution to Problem

By preparing a solid dispersion using enzalutamide and polyvinyl alcohol (hereinafter sometimes abbreviated as PVA), pH-independent solubilization and/or dissolution of enzalutamide was achieved, and its supersaturation could be maintained, and further, its bioavailability was improved by oral administration to a living body.

The present invention relates to:

[1] a pharmaceutical composition for oral administration, comprising enzalutamide and polyvinyl alcohol,
[2] the pharmaceutical composition for oral administration of [1], wherein polyvinyl alcohol has a saponification degree of 30 mol % or more and 99 mol % or less,
[3] the pharmaceutical composition for oral administration of [1] or [2], wherein polyvinyl alcohol has a polymerization degree of 50 or more and 600 or less,
[4] the pharmaceutical composition for oral administration of any one of [1] to [3], comprising a solid dispersion comprising enzalutamide and polyvinyl alcohol,
[5] the pharmaceutical composition for oral administration of any one of [1] to [4], further comprising a substance having a functional group capable of functioning as a hydrogen bond acceptor,
[6] the pharmaceutical composition for oral administration of [5], wherein the substance having a functional group capable of functioning as a hydrogen bond acceptor is polyvinyl pyrrolidone and/or copolyvidone,
[7] the pharmaceutical composition for oral administration of any one of [1] to [6], further comprising co-disintegrant,
[8] the pharmaceutical composition for oral administration of [7], wherein the co-disintegrant is a compound or two or more compounds selected from the group consisting of potassium chloride, sodium chloride, magnesium chloride, and potassium dihydrogen phosphate,
[9] the pharmaceutical composition for oral administration of [7] or [8], wherein the co-disintegrant is potassium chloride,
[10] the pharmaceutical composition for oral administration of any one of [1] to [9], further comprising disintegrant,
[11] the pharmaceutical composition for oral administration of [10], wherein the disintegrant is a compound or two or more compounds selected from the group consisting of crospovidone and low substituted hydroxypropylcellulose,
[12] the pharmaceutical composition for oral administration of [10] or [11], wherein the disintegrant is crospovidone,
[13] the pharmaceutical composition for oral administration of any one of [1] to [12], wherein the pharmaceutical composition is a tablet,
[14] the pharmaceutical composition of any one of [1] to [13], wherein enzalutamide is amorphous,
[15] a method of producing a pharmaceutical composition for oral administration comprising enzalutamide and polyvinyl alcohol,
[16] the method of producing a pharmaceutical composition for oral administration of [15], said method comprising the step of preparing a solid dispersion comprising enzalutamide and polyvinyl alcohol,
[17] the method of producing a pharmaceutical composition for oral administration of [16], wherein the solid dispersion is prepared by a hot melt extrusion method,
[18] the method of producing a pharmaceutical composition for oral administration of [16], wherein the solid dispersion is prepared by a solvent method, and
[19] use of a substance having a functional group capable of functioning as a hydrogen bond acceptor in the manufacture of a pharmaceutical composition for oral administration comprising enzalutamide and polyvinyl alcohol.

Advantageous Effects of Invention

According to the present invention, a pharmaceutical composition for oral administration in which, in a pH-independent manner, the solubility and/or the dissolution properties of enzalutamide are improved, and supersaturation is maintained can be provided. Further, a pharmaceutical composition for oral administration in which the bioavailability and the absorption rate of enzalutamide are increased can be provided.

DESCRIPTION OF EMBODIMENTS

The term "to improve solubility" as used herein means that the solubility, the dissolved concentration, or the dissolved rate of enzalutamide in a solvent is increased. More particularly, as an embodiment, with respect to the fact that the solubility of enzalutamide in water (20° C.±5° C.) is 2 μg/mL, when it is evaluated by, for example, a dissolution test of Experimental Example 3, Experimental Example 4, Experimental Example 5, Experimental Example 8, Experimental Example 11, Experimental Example 13, Experimental Example 15, or Experimental Example 16 described below, it is defined that the effect to improve the dissolved concentration is 5 times or more, 10 times or more in an embodiment, and 20 times or more in an embodiment.

The term "to improve dissolution properties" as used herein means that the dissolution rate of enzalutamide from a pharmaceutical composition is improved. More particularly, as an embodiment, when it is evaluated by a dissolution test of Experimental Example 3, Experimental Example 4, Experimental Example 5, Experimental Example 8, Experimental Example 11, Experimental Example 13, Experimental Example 15, or Experimental Example 16 described below, it is defined that the dissolution rate after 10 minutes from the beginning of the test is 60% or more, and 80% or more in an embodiment.

The term "to maintain supersaturation" as used herein means that enzalutamide is dissolved in a solution more than the solubility of enzalutamide. More particularly, as an embodiment, when a pharmaceutical composition comprising enzalutamide is evaluated by a precipitation test of Experimental Example 1 or Experimental Example 2 described below, it is defined that the time during which the change in the dissolved rate of enzalutamide in the pharmaceutical composition is within 10%, with respect to the dissolved rate at the beginning of the test, is 30 minutes or longer, 60 minutes or longer in an embodiment, and 90 minutes or longer in an embodiment.

The term "to improve oral absorbability" as used herein means, as an embodiment, to have oral absorbability, absorption rate, or PK parameters equal to, or superior to those of an XTANDI (registered trademark) Capsule, which is a preceding product, in a test subject, such as a dog, a human, or the like. In particular, it means to have properties equal to or superior to those of the XTANDI (registered trademark) Capsule in a single dose.

More particularly, it is defined that, for example, the Cmax or the AUC in a dog is 0.8 times or more, preferably 0.9 times or more, and more preferably 1 time or more, in comparison with the XTANDI (registered trademark) Capsule.

In order to be in a state of improving oral absorbability, it means that a drug in a solution is in a state that the drug is easily absorbed, such as an amorphous state or their transition states, for example, evaluated by X-ray diffraction, Raman scattering, infrared absorption, terahertz, or the like.

The term "solid dispersion" as used herein means a dispersion comprising enzalutamide and polyvinyl alcohol, wherein most enzalutamide exists in a shapeless form. The term "shapeless" as used herein means amorphous or their transition states. Shapeless enzalutamide exists as a solid solution that is homogeneously dispersed throughout polyvinyl alcohol. The term "most" as used herein means that the crystal of enzalutamide accounts for 40% or less, preferably 20% or less, when the dispersion is prepared. As another embodiment, it means that the amount of the enzalutamide crystal is 40% or less, preferably 20% or less, and more preferably 10% or less, when measured by powder X-ray diffraction, differential scanning calorimetry (DSC), or any other standard quantitative means.

The term "saponification degree" as used herein means a saponification value determined by a measurement method described in The Japanese Pharmacopoeia, Seventeenth Edition, or a measurement method correlated with the measurement method, and can be calculated by the following equation (1). In connection with this, it is desirable that the measurement method has a correlation coefficient of 0.5 or more, and 0.6 or more in an embodiment, with the measurement method described in The Japanese Pharmacopoeia, Seventeenth Edition.

Saponification degree=$m/(m+n) \times 100$     (1)

[m: number of hydroxyl groups, n: number of acetyl groups]

The term "polymerization degree" as used herein means an "average polymerization degree", and is defined as a value calculated on the basis of a viscosity value when evaluated according to the Japanese Pharmaceutical Excipients or a molecular weight measured by gel filtration or the like, or a value measured according to a measurement method correlated with the measurement method. Alternatively, it is defined as a value measured by (4) Measurement Method of Average Polymerization Degree in JIS K6726 "Testing methods for polyvinyl alcohol", or a value measured according to a measurement method correlated with the measurement method. In connection with this, it is desirable that the measurement method correlated with the measurement method of a viscosity value when evaluated according to the Japanese Pharmaceutical Excipients or gel filtration or the like is a measurement method having a correlation coefficient of 0.5 or more, and 0.6 or more in an embodiment, with the measurement method of a viscosity value when evaluated according to the Japanese Pharmaceutical Excipients or gel filtration or the like. Further, it is desirable that the measurement method correlated with (4) Measurement Method of Average Polymerization Degree in JIS K6726 "Testing methods for polyvinyl alcohol" is a measurement method having a correlation coefficient of 0.5 or more, and 0.6 or more in an embodiment, with (4) Measurement Method of Average Polymerization Degree in JIS K6726 "Testing methods for polyvinyl alcohol".

The term "stable" as used herein means to have stability against, for example, heat, light, temperature, and/or humidity. For example, after a pharmaceutical composition is allowed to stand under predetermined conditions, it is defined as an embodiment in which the percentage of a maximum related substance of enzalutamide contained in the pharmaceutical composition is a specific amount or less, or it is defined as an embodiment in which, even if a solid dispersion is prepared by heating and melting, the percentage of a maximum related substance of enzalutamide contained in the pharmaceutical composition is a specific amount or less.

For example, as an embodiment, it means that the percentage of a maximum related substance of enzalutamide after storage at 70° C. for 9 days (tightly sealed) is 0.5% or less, and 0.3% or less in an embodiment.

As an embodiment, it means that the percentage of a maximum related substance of enzalutamide, after storage at 25° C. and 60% relative humidity (hereinafter sometimes referred to as 25° C., 60% RH) for 1 month, at 25° C., 60% RH for 3 months, at 25° C., 60% RH for 6 months, at 40° C. and 75% relative humidity (hereinafter sometimes referred to as 40° C., 75% RH) for 1 month, at 40° C., 75% RH for 3 months, or at 40° C., 75% RH for 6 months, is 0.5% or less, and 0.3% or less in an embodiment.

The term "maximum related substance" as used herein means the most abundant related substance among related substances of enzalutamide. More particularly, for example, when the amount of each related substance contained in a pharmaceutical composition is measured by a high-performance liquid chromatographic method (hereinafter referred to as an HPLC method), it is defined that a related substance having the largest peak area among the obtained related substances is the maximum related substance.

The term "the amount of the maximum related substance" as used herein is defined as a percentage of the maximum related substance with respect to the total peak area of enzalutamide and its related substances, when the peak area of the maximum related substance contained in a pharmaceutical composition is measured by an HPLC method.

Enzalutamide is a poorly water-soluble drug having a solubility of 2 μg/mL in water (20° C.±5° C.). It is possible to obtain good solubility and/or good dissolution properties by applying the technology of the present invention. Further, it is possible to obtain good oral absorbability by applying the technology of the present invention.

The dose of enzalutamide can be appropriately determined depending on the individual case by taking into consideration, for example, symptoms of the disease, age of the patient, race, sex, or the like.

The daily dose is, for example, about 0.001 mg/kg to 100 mg/kg, 0.01 mg/kg to 100 mg/kg in an embodiment, and 1 mg/kg to 10 mg/kg in an embodiment, which is administered once or divided into two to four doses per day. Each lower limit and each upper limit can be arbitrarily combined as desired.

The content of enzalutamide is, for example, 0.05 mg to 10000 mg, 0.5 mg to 10000 mg in an embodiment, 5 mg to 1000 mg in an embodiment, 10 mg to 200 mg in an embodiment, and 40 mg to 160 mg in an embodiment, per pharmaceutical composition for oral administration. Each lower limit and each upper limit can be arbitrarily combined as desired.

The content ratio of enzalutamide is, for example, 1% by weight to 75% by weight, 2% by weight to 50% by weight in an embodiment, 2% by weight to 30% by weight in an embodiment, and 6.7% by weight to 50% by weight in an embodiment, with respect to the total weight of the pharmaceutical composition for oral administration. Each lower limit and each upper limit can be arbitrarily combined as desired.

Polyvinyl alcohol used in the present invention is not particularly limited, so long as it is pharmaceutically acceptable. The saponification degree of polyvinyl alcohol used in the present invention is, for example, 30 mol % or more and 99 mol % or less, preferably 55 mol % or more and less than 85 mol %, more preferably 63 mol % or more and 82 mol % or less, and still more preferably 66 mol % or more and 80 mol % or less. Each lower limit and each upper limit above (and each lower limit and each upper limit described in the Examples below) can be arbitrarily combined as desired.

The polymerization degree of polyvinyl alcohol used in the present invention is not particularly limited, so long as it is pharmaceutically acceptable.

More particularly, the polymerization degree is, for example, less than 2200, 2 or more and less than 2200 in an embodiment, 10 or more and less than 2200 in an embodiment, 100 or more and less than 2200 in an embodiment, 2 or more and 600 or less in an embodiment, 10 or more and 600 or less in an embodiment, 50 or more and 600 or less in an embodiment, and 100 or more and 500 or less in an embodiment. Each lower limit and each upper limit above (and each lower limit and each upper limit described in the Examples below) can be arbitrarily combined as desired.

Each saponification degree and each polymerization degree can be arbitrarily combined as desired, and as an embodiment, the saponification degree and the polymerization degree of polyvinyl alcohol are respectively 63 mol % or more and 82 mol % or less, and 50 or more and 600 or less.

In connection with this, polyvinyl alcohol improves the solubility and/or dissolution properties of enzalutamide, and maintains the supersaturation of enzalutamide. Further, polyvinyl alcohol has a function to improve oral absorbability of enzalutamide.

Examples of polyvinyl alcohol used in the present invention include:
GOHSENOL (registered trademark) EG-03P (The Nippon Synthetic Chemical Industry Co., Ltd., viscosity: 3.0 to 3.8 mPa·s (4% aqueous solution, 20° C.), saponification degree: 86.5 to 89.0 mol %),
GOHSENOL (registered trademark) KL-05 (The Nippon Synthetic Chemical Industry Co., Ltd., viscosity: 4.0 to 5.0 mPa·s (4% aqueous solution, 20° C.), saponification degree: 78.5 to 82.0 mol %),
GOHSENOL (registered trademark) KL-03 (The Nippon Synthetic Chemical Industry Co., Ltd., viscosity: 2.8 to 3.4 mPa·s (4% aqueous solution, 20° C.), saponification degree: 78.5 to 82.0 mol %),
GOHSENOL (registered trademark) KP-08R (The Nippon Synthetic Chemical Industry Co., Ltd., viscosity: 6.0 to 8.0 mPa·s (4% aqueous solution, 20° C.), saponification degree: 71.0 to 73.5 mol %),
GOHSENOL (registered trademark) NK-05R (The Nippon Synthetic Chemical Industry Co., Ltd., viscosity: 4.5 to 5.5 mPa·s (4% aqueous solution, 20° C.), saponification degree: 71.0 to 75.0 mol %),
GOHSENX (registered trademark) LL-810 (The Nippon Synthetic Chemical Industry Co., Ltd., viscosity: 7.0 to 10.0 mPa·s (a mixture solution of 10.0% methanol/water (1/1 weight ratio)), saponification degree: 45.0 to 51.0 mol %),
GOHSENX (registered trademark) LL-920 (The Nippon Synthetic Chemical Industry Co., Ltd., viscosity: 9.0 to 13.0 mPa·s (a mixture solution of 10.0% methanol/water (1/1 weight ratio)), saponification degree: 30.0 to 38.0 mol %),
GOHSENX (registered trademark) LL-940 (The Nippon Synthetic Chemical Industry Co., Ltd., viscosity: 20.0 to 28.0 mPa·s (a mixture solution of 10.0% methanol/water (1/1 weight ratio)), saponification degree: 34.0 to 41.0 mol %),
POVAL (registered trademark) JR-05 (JAPAN VAM & POVAL CO., LTD., viscosity: 4.5 to 6.5 mPa·s (4% aqueous solution, 20° C.), saponification degree: 70.0 to 74.0 mol %),
POVAL (registered trademark) JL-05E (JAPAN VAM & POVAL CO., LTD., viscosity: 4.0 to 6.0 mPa·s (4% aqueous solution, 20° C.), saponification degree: 80.0 to 84.0 mol %),
POVAL (registered trademark) JMR-10M (JAPAN VAM & POVAL CO., LTD., polymerization degree: 200 to 280, saponification degree: 63.0 to 67.0 mol %),
POVAL (registered trademark) JMR-10L (JAPAN VAM & POVAL CO., LTD., polymerization degree: 200 to 280, saponification degree: 30.0 to 40.0 mol %), polyvinyl alcohol (Polysciences, Inc., polymerization degree: approximately 100, saponification degree: 80 mol %), and the like.

These polyvinyl alcohols may be added alone, or as a combination of two or more polyvinyl alcohols having different saponification degrees and/or polymerization degrees.

The content ratio of the polyvinyl alcohol is not particularly limited, so long as they can improve the solubility, dissolution properties and/or oral absorbability of enzalutamide. The content ratio of polyvinyl alcohol is, for example, 2% by weight to 90% by weight, 5% by weight to 75% by weight in an embodiment, and 10% by weight to 20% by weight in an embodiment, with respect to the total weight of the pharmaceutical composition for oral administration. Each lower limit and each upper limit can be arbitrarily combined as desired. It is, for example, 20% by weight to 1000% by weight, 50% by weight to 500% by weight in an embodiment, and 150% by weight to 350% by weight in an embodiment, with respect to the weight of enzalutamide. Each lower limit and each upper limit can be arbitrarily combined as desired.

The pharmaceutical composition for oral administration of the present invention may be, for example, a solid preparation, such as tablets, capsules, granules, powder, fine granules, or the like, and tablets in an embodiment.

The pharmaceutical composition for oral administration of the present invention may comprise a solid dispersion comprising enzalutamide and the polyvinyl alcohol.

In an embodiment, enzalutamide exists as an amorphous in the pharmaceutical composition for oral administration of the present invention.

In the pharmaceutical composition for oral administration of the present invention, it may be formulated by appropriately using various pharmaceutical additives, if desired, to the extent that the desired effects of the present invention can be achieved. Such pharmaceutical additives are not particularly limited, so long as they are pharmaceutically acceptable and pharmacologically acceptable. Examples of the pharmaceutical additives include co-disintegrants, disintegrants, fillers, corrigents, effervescent agents, sweeteners, flavors, lubricants, buffers, antioxidants, surfactants, glidants, and the like.

The co-disintegrant is not particularly limited, so long as it imparts a function to achieve rapid dissolution properties of enzalutamide to the preparation.

More particularly, examples of the co-disintegrants include potassium chloride, sodium chloride, magnesium chloride, potassium dihydrogen phosphate, sodium hydrogen carbonate, potassium hydrogen phosphate, potassium sulfate, sodium sulfate, sodium carbonate, calcium chloride, and the like; and the examples include potassium chloride in an embodiment.

The co-disintegrants may be added alone, or as a combination of two or more.

The content ratio of the co-disintegrant is not particularly limited, so long as it can achieve rapid dissolution properties of enzalutamide. The content ratio of the co-disintegrant is 1% by weight to 50% by weight, 2% by weight to 40% by weight in an embodiment, and 5% by weight to 30% by weight in an embodiment, with respect to the total weight of the pharmaceutical composition for oral administration. Each lower limit and each upper limit can be arbitrarily combined as desired.

The disintegrant is not particularly limited, so long as it imparts a function to achieve rapid dissolution properties of enzalutamide to the preparation.

More particularly, examples of the disintegrants include crospovidone, low substituted hydroxypropylcellulose, crystalline cellulose, sodium carboxymethylcellulose, sodium starch glycolate, and the like; the examples include crospovidone, low substituted hydroxypropylcellulose, and the like in an embodiment; and the examples include crospovidone in an embodiment.

Examples of crospovidone include Kollidon CL (product name, BASF) and the like.

The disintegrants may be added alone, or as a combination of two or more.

The content ratio of the disintegrant is not particularly limited, so long as it can achieve rapid dissolution properties of enzalutamide. The content ratio of the disintegrant is 0.5% by weight to 30% by weight, 1% by weight to 20% by weight in an embodiment, and 2% by weight to 10% by weight in an embodiment, with respect to the total weight of the pharmaceutical composition for oral administration. Each lower limit and each upper limit can be arbitrarily combined as desired.

Examples of the fillers include lactose, sucrose, D-mannitol, D-sorbitol, starch, pregelatinized starch, dextrin, gum arabic, pullulan, light anhydrous silicic acid, synthetic aluminum silicate, magnesium aluminate metasilicate, and the like.

Examples of the corrigents include citric acid, tartaric acid, malic acid, and the like.

Examples of the effervescent agents include sodium bicarbonate, and the like.

Examples of the sweeteners include saccharin sodium, dipotassium glycyrrhizinate, aspartame, stevia, thaumatin, and the like.

Examples of the flavors include lemon, lemon-lime, orange, menthol, and the like.

Examples of the lubricants include magnesium stearate, calcium stearate, stearic acid, hydrogenated oil, and the like.

Examples of the buffers include citric acid, succinic acid, fumaric acid, tartaric acid, ascorbic acid, and salts thereof; glutamic acid, glutamine, glycine, aspartic acid, alanine, arginine, and salts thereof; magnesium oxide, zinc oxide, magnesium hydroxide, phosphoric acid, boric acid, and salts thereof; and the like.

Examples of the antioxidants include ascorbic acid, dibutyl hydroxytoluene, propyl gallate, and the like.

Examples of the surfactants include polysorbate 80, sodium lauryl sulfate, polyoxyethylene hydrogenated castor oil, and the like.

Examples of the glidants include light anhydrous silicic acid, and the like.

These pharmaceutical additives may be appropriately added alone, or as a combination of two or more, in appropriate amounts. With respect to the content ratios of the pharmaceutical additives, each pharmaceutical additive may be contained in an amount such that the desired effects of the present invention may be achieved.

A "substance having a functional group capable of functioning as a hydrogen bond acceptor" may be further added.

The substance having a functional group capable of functioning as a hydrogen bond acceptor is not particularly limited, so long as it is a polymer which inhibits hydrogen bonds between polyvinyl alcohol molecules, which has a function to increase amorphous properties of polyvinyl alcohol, or which improves the stability and dissolution properties of enzalutamide. Examples thereof include substances with negative atoms, such as fluorine, oxygen, nitrogen, or the like; polyvinylpyrrolidone and copolyvidone in an embodiment; and copolyvidone in an embodiment.

Examples of copolyvidone include Kollidon VA64 (product name, BASF), Kollidon VA64 Fine (product name, BASF), and the like.

Examples of polyvinylpyrrolidone include Kollidon 30 (product name, BASF), and the like.

The substance having a functional group capable of functioning as a hydrogen bond acceptor may be added to the pharmaceutical composition for oral administration of the present invention in any arbitrary way, to the extent that the desired effects of the present invention can be achieved.

Examples of such an embodiment include an embodiment in which the substance having a functional group capable of functioning as a hydrogen bond acceptor is added to a solid dispersion comprising enzalutamide and polyvinyl alcohol.

The substance having a functional group capable of functioning as a hydrogen bond acceptor may be added alone, or as a combination of two or more.

The content ratio of the substance having a functional group capable of functioning as a hydrogen bond acceptor is not particularly limited, so long as rapid dissolution properties of enzalutamide can be achieved, and a stable pharmaceutical composition ca be obtained. The content ratio of the substance having a functional group capable of functioning as a hydrogen bond acceptor is, for example, 1% by weight to 40% by weight, 2% by weight to 30% by weight in an embodiment, 5% by weight to 25% by weight in an embodiment, 10% by weight to 20% by weight in an embodiment, and 6.7% by weight to 40% by weight in an embodiment, with respect to the total weight of the pharmaceutical composition for oral administration. Each lower limit and each upper limit can be arbitrarily combined as desired. With respect to the weight of enzalutamide, the content ratio of the substance having a functional group capable of functioning as a hydrogen bond acceptor is, for example, 1% by weight to 1000% by weight, 50% by weight to 500% by weight in an embodiment, and 100% by weight to 300% by weight in an embodiment. Each lower limit and each upper limit can be arbitrarily combined as desired. With respect to the weight of polyvinyl alcohol, the content ratio of the substance having a functional group capable of functioning as a hydrogen bond acceptor is, for example, 10% by weight to 1000% by weight, 20% by weight to 200% by weight in an embodiment, and 30% by weight to 150% by weight in an embodiment. Each lower limit and each upper limit can be arbitrarily combined as desired.

The pharmaceutical composition for oral administration of the present invention can be produced in accordance with known methods including, for example, amorphization of enzalutamide, mixing, granulation, forming (tableting), film coating, and the like.

The process of manufacturing the pharmaceutical composition for oral administration of the present invention will be explained below.

Amorphization Step

Examples of a method of amorphizing enzalutamide include a method of preparing a solid dispersion. The method of preparing a solid dispersion of enzalutamide and polyvinyl alcohol is not particularly limited, so long as it is a conventional method of preparing a solid dispersion. Examples of the method include a solvent method, a hot melt extrusion method, and the like.

(I) Solvent Method

Examples of the solvent method include a method in which after enzalutamide and polyvinyl alcohol are dissolved and/or suspended in a solvent, the solvent is removed; and the like.

The solvent used is not particularly limited, so long as enzalutamide and polyvinyl alcohol can be dissolved and/or suspended in the solvent. More particularly, examples of the solvent include methanol, dichloromethane, water, ethanol, acetone, propylene glycol, dimethyl sulfoxide, and the like; and the examples include methanol and water in an embodiment. These solvents can be appropriately used alone, or as a combination of two or more, in appropriate amounts.

Examples of a method of removing the solvent include spray drying, evaporation, freeze drying, and the like; and the examples include spray drying in an embodiment.

Examples of steps for preparing a spray solution comprising enzalutamide, which is used in the spray drying, include the steps of:
(1) dissolving and/or suspending polyvinyl alcohol in water,
(2) adding methanol to (1) to prepare a mixed solution, and
(3) adding enzalutamide to the mixed solution of (2) to prepare a spray solution.

An apparatus for spray drying is not particularly limited, so long as enzalutamide can be formed into an amorphous form, or a solid dispersion of enzalutamide and polyvinyl alcohol can be obtained. Examples of the apparatus include a spray dryer. The conditions for spray drying are not particularly limited, so long as the solid dispersion of enzalutamide and polyvinyl alcohol can be obtained. The outlet temperature of the spray dryer is, for example, 20° C. to 80° C.

A method for drying is not particularly limited, so long as it is a conventional method in which it can be pharmaceutically dried. Examples of an apparatus include a forced-air dryer, a dryer under reduced pressure, a vacuum dryer, a fluidized bed dryer, and the like.

(II) Hot Melt Extrusion Method

In the hot melt extrusion method, enzalutamide and polyvinyl alcohol are heated and melted, and then, cooled.

The temperature during heating and melting can be appropriately set in accordance with the melting point of enzalutamide, or the glass transition temperature of polyvinyl alcohol. The temperature is, for example, 100° C. to 220° C. The temperature during heating and melting can be appropriately set in consideration of the solubility, dissolution properties, supersaturation maintaining ability, and/or stability of enzalutamide.

An apparatus is not particularly limited, so long as enzalutamide can be formed into an amorphous form, or the solid dispersion of enzalutamide and polyvinyl alcohol can be obtained. Examples thereof include a twin-screw extruder.

As a carrier for solid dispersion, the "substance having a functional group capable of functioning as a hydrogen bond acceptor" may be further added.

A method for pulverization is not particularly limited, so long as it is a conventional method in which it can be pharmaceutically pulverized. Examples of an apparatus include an impact mill (Hosokawa Micron Corporation; Fine Impact Mill), a dry & wet mill (Powrex Corporation: Comil), a cutting mill granulator (Dalton Corporation; Power Mill), and the like.

Mixing Step

A mixing method is not particularly limited, so long as it is a conventional method in which each component can be pharmaceutically and uniformly mixed. Examples of an apparatus include a V-type mixer, a ribbon-type mixer, a container mixer, a high speed mixer, and the like.

Granulation Step

A granulation method is not particularly limited, so long as it is a conventional method in which granulation can be pharmaceutically carried out. Examples of an apparatus include a fluidized bed granulator, a melting agitation granulator, a high shear granulator, a milling (pulverization) and granulating machine, an extrusion granulator, a tumbling fluidized bed granulator, a spray granulator, a dry granulator, a twin-screw extruder, and the like; and a dry granulator in an embodiment.

Forming (Tableting) Step

A forming method is not particularly limited, so long as it is a conventional method in which forming can be pharmaceutically carried out. Examples of an apparatus include a rotary tableting machine, a single punch tableting machine, an oil press, and the like.

In the forming step, for example, a method in which a granulated product containing the solid dispersion of enzalutamide, or a mixed product (a mixed product before compression-molding, in particular, a mixed product before tableting) prepared by mixing the granulated product with various pharmaceutical additives, such as a lubricant, is compression-molded to form tablets; a direct tableting method in which the solid dispersion of enzalutamide is mixed with appropriate pharmaceutical additives, and the mixture is compression-molded to obtain tablets; or the like, may be used.

Film Coating Step

A film coating method is not particularly limited, so long as it is a conventional method in which film coating can be pharmaceutically carried out.

Examples of an apparatus include a pan coating machine, a fluidized bed coating machine, and the like.

Base materials for film coating and coloring agents may be appropriately added alone, or as a combination of two or more, in appropriate amounts.

If desired, after the film coating, the coated product may be dried. The drying method is not particularly limited, so long as it is a conventional method in which drying can be pharmaceutically carried out. Examples of an apparatus include a pan coating machine, a fluidized bed coating machine, and the like. The conditions for drying are not particularly limited, so long as the conditions are appropriately determined depending on the stability of the preparation.

The present invention includes, in a pharmaceutical composition for oral administration comprising enzalutamide and polyvinyl alcohol, a use of a substance having a functional group capable of functioning as a hydrogen bond acceptor in the manufacture of the pharmaceutical composition for oral administration, which is stable.

With respect to the terms "enzalutamide", "polyvinyl alcohol", and "a substance having a functional group capable of functioning as a hydrogen bond acceptor", which are used in the use of the present invention, the explanations therefor described in the pharmaceutical composition for oral administration of the present invention can be directly applied.

EXAMPLES

Enzalutamide, which was used in the Examples below, had been prepared in accordance with a method described in WO 2011/106570.

The present invention will now be further illustrated by, but is by no means limited to, the following Examples, Comparative Examples, and Experimental Examples.

<<Experimental Example 1>> Precipitation Test

The following precipitation test was carried out in order to confirm the effects of polyvinyl alcohols with different saponification degrees to improve the solubility of enzalutamide and to maintain supersaturation. As the polyvinyl alcohols, POVAL (JMR-10M, JAPAN VAM & POVAL CO., LTD., hereinafter sometimes abbreviated as "A1"), GOHSENOL (NK-05R, The Nippon Synthetic Chemical Industry Co., Ltd., hereinafter sometimes abbreviated as "A2"), GOHSENOL (KL-05, The Nippon Synthetic Chemical Industry Co., Ltd., hereinafter sometimes abbreviated as "A3"), POVAL (PE-05JPS, JAPAN VAM & POVAL CO., LTD., hereinafter sometimes abbreviated as "B1"), POVAL (JT-05, JAPAN VAM & POVAL CO., LTD., hereinafter sometimes abbreviated as "B2"), and GOHSENOL (NL-05, The Nippon Synthetic Chemical Industry Co., Ltd., hereinafter sometimes abbreviated as "B3") were used. The saponification degrees and the polymerization degrees of the polyvinyl alcohols used in the test are shown in Table 1. After 200 mg of each polyvinyl alcohol was previously dissolved in 500 mL of water, 1 mL of an acetone solution of enzalutamide (containing 40 mg equivalent of enzalutamide) adjusted to a concentration of 40 mg/mL was added thereto, and a precipitation test was carried out in accordance with a Dissolution Test, a paddle method of the Japanese Pharmacopoeia at a paddle rotation speed of 50 rpm under a constant temperature of 37° C. The ultraviolet absorbance of enzalutamide was measured at 260 nm. The dissolved rate was calculated when an absorbance of 1.579 in a 5-mm cell was regarded as 100%.

TABLE 1

|  | A1 | A2 | A3 | B1 | B2 | B3 |
|---|---|---|---|---|---|---|
| Saponification degree (mol %) | 66 | 73 | 80 | 88 | 94 | 99 |
| Polymerization degree | 260 | 500 | 500 | 500 | 500 | 500 |

Figure 1:
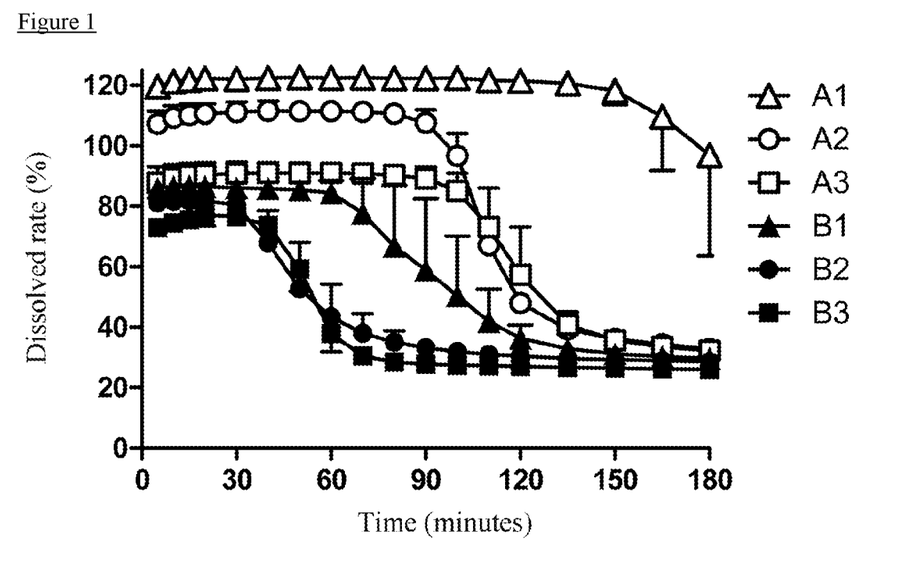
FIG. 1 is a graph showing the results of a precipitation test in Experimental Example 1.

The test results are shown in FIG. 1. Each test was repeated three times, and the average values are shown. In the saponification value range (66 mol % to 99 mol %) of the polyvinyl alcohols used in Experimental Example 1, as the saponification degree was lower, the solubility was improved and the supersaturation was maintained. In particular, in a saponification value range of 66 mol % to 80 mol %, it was clarified that supersaturation could be highly maintained in addition to a high dissolved rate.

<<Experimental Example 2>> Precipitation Test

The following precipitation test was carried out in order to confirm the effects of polyvinyl alcohols with different polymerization degrees to improve the solubility of enzalutamide and to maintain supersaturation. As the polyvinyl alcohols, polyvinyl alcohol having a saponification degree of 80 and a polymerization degree of approximately 100 (manufactured by Polysciences, Inc., hereinafter sometimes abbreviated as "A4"), polyvinyl alcohol having a saponification degree of 80 and a polymerization degree of approximately 300 (GOHSENOL, KL-03, The Nippon Synthetic Chemical Industry Co., Ltd., hereinafter sometimes abbreviated as "A5"), and polyvinyl alcohol having a saponification degree of 80 and a polymerization degree of approximately 2200 (GOHSENOL, KH-17, The Nippon Synthetic Chemical Industry Co., Ltd., hereinafter sometimes abbreviated as "B4") were used. The saponification degrees and the polymerization degrees of the polyvinyl alcohols used in the test are shown in Table 2. After 200 mg of each polyvinyl alcohol was previously dissolved in 500 mL of water, 1 mL of an acetone solution of enzalutamide (containing 40 mg equivalent of enzalutamide) adjusted to a concentration of 40 mg/mL was added thereto, and a precipitation test was carried out in accordance with a Dissolution Test, a paddle method of the Japanese Pharmacopoeia at a paddle rotation speed of 50 rpm under a constant temperature of 37° C. The ultraviolet absorbance of enzalutamide was measured at 260 nm. The dissolved rate was calculated when an absorbance of 1.579 in a 5-mm cell was regarded as 100%.

TABLE 2

|  | A4 | A5 | B4 |
|---|---|---|---|
| Saponification degree (mol %) | 80 | 80 | 80 |
| Polymerization degree | 100 | 300 | 2200 |

Figure 2:
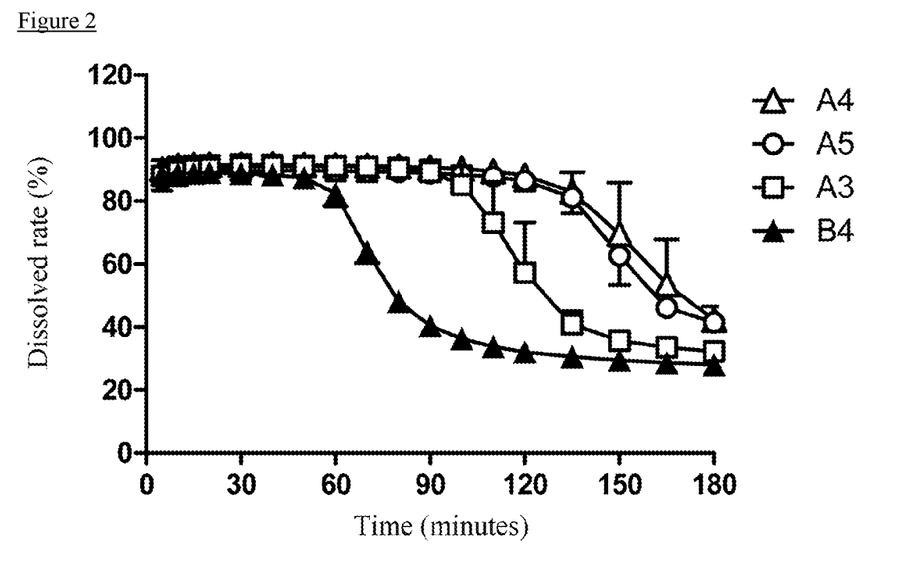
FIG. 2 is a graph showing the results of a precipitation test in Experimental Example 2.

The test results are shown in FIG. 2. Each test was repeated three times, and the average values are shown. FIG. 2 includes the result of A3 in Experimental Example 1. In the polymerization value range (100 to 2200) of the polyvinyl alcohols used in Experimental Example 2, as the polymerization degree was lower, the dissolved rate was improved. In particular, in a polymerization value range of 100 to 500, it was clarified that supersaturation could be highly maintained in addition to a high dissolved rate.

Example 1

In 40 mL of water, 3 g of "A2" was stirred until dissolved. To a mixed solution prepared by further adding 160 mL of methanol to the "A2" solution, 1 g of enzalutamide was added and stirred until dissolved to prepare a spray solution. The spray solution was spray-dried with a spray dryer (Niro SD-Micro™ Spray Dryer, GEA) to obtain a pharmaceutical composition (a solid dispersion) of Example 1.

Example 2

In 280 mL of water, 10 g of "A6" (polyvinyl alcohol prepared by purifying "A5" by The Nippon Synthetic Chemical Industry Co., Ltd. to reduce the amount of residual solvent, hereinafter sometimes abbreviated as "A6") was stirred until dissolved. To a mixed solution prepared by further adding 1120 mL of methanol to the "A6" solution, 10 g of enzalutamide was added and stirred until dissolved to prepare a spray solution. The spray solution was spray-dried with a spray dryer (Niro SD-Micro™ Spray Dryer, GEA) to obtain a pharmaceutical composition (a solid dispersion) of Example 2. The saponification degree and the polymerization degree of "A6" used in the following Examples are shown in Table 3.

Example 3

In 2356.8 g of water, 120 g of "A6" was stirred until dissolved. To a mixed solution prepared by further adding 7463.2 g of methanol to the "A6" solution, 60 g of enzalutamide was added and stirred until dissolved to prepare a spray solution. The spray solution was spray-dried with a spray dryer (QSD-0.8-CC, GEA) to obtain a pharmaceutical composition (a solid dispersion) of Example 3. It was confirmed by X-ray diffraction that the pharmaceutical composition (a solid dispersion) of Example 3 was in an amorphous state.

Example 4

In 2342.4 g of water, 180 g of "A6" was stirred until dissolved. To a mixed solution prepared by further adding 7417.7 g of methanol to the "A6" solution, 60 g of enzalutamide was added and stirred until dissolved to prepare a spray solution. The spray solution was spray-dried with a spray dryer (QSD-0.8-CC, GEA) to obtain a pharmaceutical composition (a solid dispersion) of Example 4. It was confirmed by X-ray diffraction that the pharmaceutical composition (a solid dispersion) of Example 4 was in an amorphous state.

Example 5

In 3513.6 g of water, 270 g of GOHSENOL (EG-05P, The Nippon Synthetic Chemical Industry Co., Ltd., hereinafter sometimes abbreviated as "B5") was stirred while heating until dissolved. To a mixed solution prepared by further adding 11126.4 g of methanol to the "B5" solution, 90 g of enzalutamide was added and stirred until dissolved to prepare a spray solution. The spray solution was spray-dried with a spray dryer (QSD-0.8-CC, GEA) to obtain a pharmaceutical composition (a solid dispersion) of Example 5. The saponification degree and the polymerization degree of "B5" used in tests are shown in Table 3.

TABLE 3

|  | A6 | B5 |
| --- | --- | --- |
| Saponification degree (mol %) | 81 | 88 |
| Polymerization degree | 300 | 600 |

Example 6

In 96 mL of water, 3 g of "B2" was stirred while heating until dissolved. To a mixed solution prepared by further adding 224 mL of methanol to the "B2" solution, 1 g of enzalutamide was added and stirred until dissolved to prepare a spray solution. The spray solution was spray-dried with a spray dryer (Niro SD-Micro™ Spray Dryer, GEA) to obtain a pharmaceutical composition (a solid dispersion) of Example 6.

Example 7

In 175 mL of water, 3 g of "B3" was stirred while heating until dissolved. To a mixed solution prepared by further adding 325 mL of methanol to the "B3" solution, 1 g of enzalutamide was added and stirred until dissolved to prepare a spray solution. The spray solution was spray-dried with a spray dryer (Niro SD-Micro™ Spray Dryer, GEA) to obtain a pharmaceutical composition (a solid dispersion) of Example 7.

<<Experimental Example 3>> Dissolution Test

A dissolution test of the pharmaceutical compositions (solid dispersions) prepared in Examples 1 to 7 (containing 80 mg equivalent of enzalutamide) was carried out. The formulation of each pharmaceutical composition is shown in Table 4. Powder mixed with the same amount of mannitol (PEARLITOL 200SD) as that of each pharmaceutical composition (solid dispersion) was used for the test. The dissolution test was carried out using water (test fluid volume: 500 mL, fluid temperature: 37° C.) as a dissolution test fluid in accordance with a Dissolution Test, a paddle method of the Japanese Pharmacopoeia at a paddle rotation speed of 50 rpm (250 rpm for 0 to 3 minutes from the beginning of the test, and 200 rpm for 3 to 5 minutes). The ultraviolet absorbance of enzalutamide was measured at 260 nm. The dissolution rate was calculated when an absorbance of 0.6316 in a 1-mm cell was regarded as 100%.

TABLE 4

|  | Ex. 1 | Ex. 2 | Ex. 3 | Ex. 4 | Ex. 5 | Ex. 6 | Ex. 7 |
| --- | --- | --- | --- | --- | --- | --- | --- |
| Enzalutamide | 80 | 80 | 80 | 80 | 80 | 80 | 80 |
| A2 | 240 | — | — | — | — | — | — |
| A6 | — | 80 | 160 | 240 | — | — | — |
| B5 | — | — | — | — | 240 | — | — |
| B2 | — | — | — | — | — | 240 | — |
| B3 | — | — | — | — | — | — | 240 |

(Unit: mg)

The dissolution rates after 10 minutes from the beginning of the dissolution test ($D_{10min}$) are shown in Table 5. High dissolution rates of 60% or higher were obtained in the pharmaceutical compositions (solid dispersions) of Examples 1 to 4, using polyvinyl alcohol having a saponification degree of 81 mol % or less. Among the pharmaceutical compositions (solid dispersions) of Examples 2 to 4 using "A6", extremely high dissolution rates of 80% or higher were obtained in the pharmaceutical compositions (solid dispersions) containing "A6" two or more times to enzalutamide. In the pharmaceutical compositions (solid dispersions) of Examples 5 to 7, using polyvinyl alcohol having a saponification degree of 88 mol % or more, whereas the solubility of enzalutamide in water (20° C.±5° C.) was 2 µg/mL, even the pharmaceutical composition of Example 7 showed a dissolved concentration of 15.2 µg/mL (=80 mg×9.5%/500 mL), and an improvement effect of 7 times or more in the dissolved concentration was observed. Similarly, the pharmaceutical compositions of Examples 5 and 6 respectively showed dissolved concentrations of 22.56 µg/mL (11.28 times) and 41.6 µg/mL (20.8 times), and improvement effects of 10 times or more in the dissolved concentration were observed.

TABLE 5

|  | Ex. 1 | Ex. 2 | Ex. 3 | Ex. 4 | Ex. 5 | Ex. 6 | Ex. 7 |
| --- | --- | --- | --- | --- | --- | --- | --- |
| $D_{10\ min}$ (%) | 93.9 | 70.3 | 97.7 | 94.2 | 14.1 | 26.0 | 9.5 |

Example 8

In 120 mL of water, 10 g of "A6" was stirred until dissolved. To a mixed solution prepared by further adding 480 mL of methanol to the "A6" solution, 2 g of enzalutamide was added and stirred until dissolved to prepare a spray solution. The spray solution was spray-dried with a spray dryer (Niro SD-Micro™ Spray Dryer, GEA) to obtain a pharmaceutical composition (a solid dispersion) of Example 8.

<<Experimental Example 4>> Dissolution Test

A dissolution test of the pharmaceutical composition (solid dispersion) prepared in Example 8 (containing 80 mg equivalent of enzalutamide) was carried out. The formulation of Example 8 is shown in Table 6. Powder mixed with the same amount of mannitol (PEARLITOL 200SD) as that of the pharmaceutical composition (solid dispersion) was used for the test. The dissolution test was carried out, using 500 mL of water, 500 mL of 1st fluid for disintegration test of the Japanese Pharmacopoeia (JP1st), and a solution prepared by dissolving 895 mg of SIF Powder (Simulated Intestinal Fluid Powder, Biorelevant.com) in 500 mL of 2nd fluid for disintegration test of the Japanese Pharmacopoeia (JP2nd+SIF) as three types of dissolution test fluids, in accordance with a Dissolution Test, a paddle method of the Japanese Pharmacopoeia at a paddle rotation speed of 50 rpm (250 rpm for 0 to 3 minutes from the beginning of the test, and 200 rpm for 3 to 5 minutes) under a fluid temperature of 37° C. The ultraviolet absorbance of enzalutamide was measured at 260 nm. The dissolution rate was calculated when an absorbance of 0.6316 in a 1-mm cell was regarded as 100%.

TABLE 6

|  | Ex. 8 |
|---|---|
| Enzalutamide | 80 |
| A6 | 400 |

(Unit: mg)

The dissolution rate after 10 minutes from the beginning of the dissolution test ($D_{10min}$) is shown in Table 7. Extremely high dissolution rates of 80% or higher were observed in any test fluid of water, JP1st, and JP2nd+SIF. Since the pharmaceutical composition (solid dispersion) of the present invention, which can be prepared using polyvinyl alcohol, is not pH-dependent, it is expected that it can be dissolved even in a low pH environment, such as in the stomach, and that a rapid drug absorbability can be obtained.

TABLE 7

|  | Water | JP1st | JP2nd + SIF |
|---|---|---|---|
| $D_{10\ min}$ (%) | 98.8 | 91.8 | 94.4 |

Comparative Example 1

After 20 g of a copolymer of polyvinyl alcohol, acrylic acid, and methyl methacrylate (POVACOAT Type F, Daido Chemical Corporation) was mixed with 4 g of enzalutamide, 22.5 g of the mixture was melted and kneaded using an extruder (DSM Xplore Pharma Micro Extruder), and pulverized to obtain a pharmaceutical composition (solid dispersion) of Comparative Example 1.

<<Experimental Example 5>> Dissolution Test

A dissolution test of the pharmaceutical compositions (solid dispersions) prepared in Example 4 and Comparative Example 1 (containing 160 mg equivalent of enzalutamide) was carried out. The formulation of each pharmaceutical composition is shown in Table 8. Powder mixed with the same amount of mannitol (PEARLITOL 200SD) as that of each pharmaceutical composition (solid dispersion) was used for the test. The dissolution test was carried out using water (test fluid volume: 500 mL, fluid temperature: 37° C.) as a dissolution test fluid in accordance with a Dissolution Test, a paddle method of the Japanese Pharmacopoeia at a paddle rotation speed of 50 rpm. After the powder mixed with mannitol was previously filled in a syringe, 20 mL of the dissolution test fluid was suctioned into the syringe. The powder was dispersed by shaking, and the syringe was put into a dissolution tester to start the test. The ultraviolet absorbance of enzalutamide was measured at 260 nm. The dissolution rate was calculated when an absorbance of 1.2632 in a 1-mm cell was regarded as 100%.

TABLE 8

|  | Ex. 4 | Comp. 1 |
|---|---|---|
| Enzalutamide | 160 | 160 |
| A6 | 480 | — |
| POVACOAT | — | 800 |

(Unit: mg)

The dissolution rates after 10 minutes from the beginning of the dissolution test ($D_{10min}$) are shown in Table 9. Even when compared to POVACOAT, "A6" showed a high effect to improve solubility. In other words, a high effect to improve solubility was obtained to select polyvinyl alcohol having a low saponification degree.

TABLE 9

|  | Ex. 4 | Comp. 1 |
|---|---|---|
| $D_{10\ min}$ (%) | 103.3 | 11.2 |

<<Experimental Example 6>> Oral Absorption Test in Dog

Suspensions of the pharmaceutical compositions (solid dispersions) prepared in Examples 2, 3, and 5, and XTANDI (registered trademark) Capsules (each containing 160 mg equivalent of enzalutamide) were orally administered to five male beagle dogs separately under fasting conditions. The formulation of each pharmaceutical composition (solid dispersion) is shown in Table 10. After the administration, blood was periodically collected, and the concentration of unchanged enzalutamide in plasma obtained by centrifugation was measured. The dogs were in a fasting state for more than 16 hours prior to the scheduled administration time. The dogs were subjected to pentagastrin treatment (intramuscular administration in the buttocks; 30 minutes before administration, and 30 and 90 minutes after administration) to control the intragastric pH to acidity, and the test was carried out.

TABLE 10

|  | Ex. 2 | Ex. 3 | Ex. 5 |
|---|---|---|---|
| Enzalutamide | 160 | 160 | 160 |
| A6 | 160 | 320 | — |
| B5 | — | — | 480 |

(Unit: mg)

The maximum plasma concentration of an unchanged form (Cmax), the area under the plasma concentration time curve of an unchanged form from 0 to 24 hours (AUC), and the time to reach the maximum plasma concentration of an unchanged form (Tmax) of the suspensions of the pharmaceutical compositions (solid dispersions) of Examples 2, 3, and 5, and the XTANDI (registered trademark) Capsules, and the ratios thereof to the values of the XTANDI Capsules (GMR) are shown in Table 11. In Example 5 containing "B5" having a saponification degree of 88 mol % in 3 times the amount of enzalutamide, both Cmax and AUC showed the same absorbabilities as those of the XTANDI (registered trademark) Capsules. In Examples 2 and 3 containing "A6" having a saponification degree of 81 mol % in 1 time and 2 times the amount of enzalutamide, respectively, both Cmax and AUC showed absorbabilities higher than those of the XTANDI (registered trademark) Capsules, and a high absorption was obtained. Further, in Examples 2 and 3, Tmax was shorter than that of the XTANDI (registered trademark) Capsules, and a rapid absorbability was observed.

TABLE 11

|  | XTANDI capsules | Ex. 2 | Ex. 3 | Ex. 5 |
|---|---|---|---|---|
| Cmax μg/mL | 20.9 ± 3.8 | 21.4 ± 4.7 | 22.4 ± 2.7 | 19.2 ± 3.3 |
| GMR | — | 1.02 | 1.08 | 0.92 |
| AUC μg/mL · h | 367.7 ± 79.7 | 377.8 ± 112.1 | 389.2 ± 71.3 | 348.8 ± 72.9 |
| GMR | — | 1.01 | 1.06 | 0.95 |
| Tmax h | 7.80 ± 1.79 | 3.90 ± 4.04 | 4.80 ± 3.03 | 9.00 ± 2.24 |

Comparative Example 2

After 15 g of polyvinylpyrrolidone (Kollidon 30, BASF) was mixed with 5 g of enzalutamide, 18 g of the mixture was melted and kneaded using an extruder (DSM Xplore Pharma Micro Extruder), and pulverized to obtain a pharmaceutical composition (solid dispersion) of Comparative Example 2.

<<Experimental Example 7>> Oral Absorption Test in Dog

Suspensions of the pharmaceutical compositions (solid dispersions) prepared in Example 4 and Comparative Example 2, and XTANDI (registered trademark) Capsules (each containing 160 mg equivalent of enzalutamide) were orally administered to four male beagle dogs separately under fasting conditions. The formulation of each pharmaceutical composition is shown in Table 12. The test was carried out under the same test conditions as those in Experimental Example 6.

TABLE 12

|  | Ex. 4 | Comp. 2 |
|---|---|---|
| Enzalutamide | 160 | 160 |
| A6 | 480 | — |
| Polyvinylpyrrolidone | — | 480 |

(Unit: mg)

The maximum plasma concentration of an unchanged form (Cmax), the area under the plasma concentration time curve of an unchanged form from 0 to 24 hours (AUC), and the time to reach the maximum plasma concentration of an unchanged form (Tmax) of the suspensions of the pharmaceutical compositions (solid dispersions) of Example 4 and Comparative Example 2, and the XTANDI (registered trademark) Capsules, and the ratios thereof to the values of the XTANDI Capsules (GMR) are shown in Table 13. Whereas both Cmax and AUC were lower than those of the XTANDI (registered trademark) Capsules in Comparative Example 2 containing polyvinylpyrrolidone (generally used as a base material for solid dispersion) in 3 times the amount of enzalutamide, both Cmax and AUC were higher than those of the XTANDI (registered trademark) Capsules in Example 4 containing "A6" in 3 times the amount of enzalutamide, and a high absorbability was obtained. Further, in Example 4, as similar to Examples 2 and 3, Tmax was shorter than that of the XTANDI (registered trademark) Capsules, and a rapid absorbability was observed.

TABLE 13

|  | XTANDI capsules | Ex. 4 | Comp. 2 |
|---|---|---|---|
| Cmax μg/mL | 16.0 ± 6.6 | 16.5 ± 4.8 | 11.4 ± 4.3 |
| GMR | — | 1.07 | 0.73 |

TABLE 13-continued

|  | XTANDI capsules | Ex. 4 | Comp. 2 |
|---|---|---|---|
| AUC μg/mL · h | 266.9 ± 101.6 | 281.1 ± 100.1 | 193.9 ± 77.1 |
| GMR | — | 1.06 | 0.73 |
| Tmax h | 8.00 ± 2.83 | 4.88 ± 4.84 | 5.75 ± 3.86 |

Example 9

After 300 g of enzalutamide, 900 g of "A6", and 300 g of polyvinylpyrrolidone (Kollidon 30, BASF) were mixed, the mixture was melted and kneaded using an extruder (KEX-25, Kurimoto, Ltd.), and pulverized to obtain a pharmaceutical composition (solid dispersion) of Example 9. It was confirmed by X-ray diffraction that the solid dispersion of Example 9 was in an amorphous state.

Example 10

After 200 g of enzalutamide, 400 g of "A6", and 400 g of copolyvidone (Kollidon VA64, BASF) were mixed, the mixture was melted and kneaded using an extruder (KEX-25, Kurimoto, Ltd.), and pulverized to obtain a pharmaceutical composition (solid dispersion) of Example 10.

<<Experimental Example 8>> Dissolution Test

A dissolution test of the pharmaceutical compositions (solid dispersions) prepared in Examples 9 and 10 (containing 160 mg equivalent of enzalutamide) was carried out. The formulation of each pharmaceutical composition (solid dispersion) is shown in Table 14. Powder mixed with the same amount of mannitol (PEARLITOL 200SD) as that of each pharmaceutical composition (solid dispersion) was used for the test. The dissolution test was carried out using water (test fluid volume: 500 mL, fluid temperature: 37° C.) as a dissolution test fluid in accordance with a Dissolution Test, a paddle method of the Japanese Pharmacopoeia at a paddle rotation speed of 50 rpm. After the powder mixed with mannitol was previously filled in a syringe, 20 mL of the dissolution test fluid was suctioned into the syringe. The powder was dispersed by shaking, and the syringe was put into a dissolution tester to start the test. The ultraviolet absorbance of enzalutamide was measured at 260 nm. The dissolution rate was calculated when an absorbance of 1.2632 in a 1-mm cell was regarded as 100%.

TABLE 14

|  | Ex. 9 | Ex. 10 |
|---|---|---|
| Enzalutamide | 160 | 160 |
| A6 | 480 | 320 |
| Polyvinylpyrrolidone | 160 | — |
| Copolyvidone | — | 320 |

(Unit: mg)

The dissolution rates after 10 minutes from the beginning of the dissolution test ($D_{10min}$) are shown in Table 15. Extremely high dissolution rates of 80% or higher were obtained in both Examples 9 and 10.

TABLE 15

|  | Ex. 9 | Ex. 10 |
| --- | --- | --- |
| $D_{10\ min}$ (%) | 108.1 | 110.8 |

<<Experimental Example 9>> Oral Absorption Test in Dog

Suspensions of the pharmaceutical compositions (solid dispersions) prepared in Examples 9 and 10, and XTANDI (registered trademark) Capsules (each containing 160 mg equivalent of enzalutamide) were orally administered to five male beagle dogs separately under fasting conditions. The formulation of each pharmaceutical composition is shown in Table 14. The test was carried out under the same test conditions as those in Experimental Example 6.

The maximum plasma concentration of an unchanged form (Cmax), the area under the plasma concentration time curve of an unchanged form from 0 to 24 hours (AUC), and the time to reach the maximum plasma concentration of an unchanged form (Tmax) of the suspensions of the pharmaceutical compositions of Examples 9 and 10, and the XTANDI (registered trademark) Capsules, and the ratios thereof to the values of the XTANDI Capsules (GMR) are shown in Table 16. Cmax in Example 9, and both Cmax and AUC in Example 10 were higher than those of the XTANDI (registered trademark) Capsules, and a high absorbability was obtained. Further, in Examples 9 and 10, Tmax was shorter than that of the XTANDI (registered trademark) Capsules, and a rapid absorbability was observed.

TABLE 16

|  |  | XTANDI capsules | Ex. 9 | Ex. 10 |
| --- | --- | --- | --- | --- |
| Cmax | µg/mL | 20.9 ± 3.8 | 26.6 ± 2.9 | 23.6 ± 6.2 |
|  | GMR | — | 1.29 | 1.11 |
| AUC | µg/mL · h | 367.7 ± 79.7 | 360.6 ± 17.2 | 400.8 ± 129.5 |
|  | GMR | — | 1.00 | 1.07 |
| Tmax | h | 7.80 ± 1.79 | 2.80 ± 4.07 | 3.90 ± 3.78 |

<<Experimental Example 10>> Measurement of Amount of Maximum Related Substance

With respect to the pharmaceutical compositions (solid dispersions) prepared in Examples 9 and 10 (each containing 80 mg equivalent of enzalutamide), the amount of the maximum related substance of enzalutamide was measured by an HPLC method.

The measurement of the amount of the maximum related substance was carried out under the following conditions:
 As an HPLC column, Zorbax SB-CN, particle size: 5 µm, 4.6 mm (inner diameter)×150 mm (manufactured by Agilent) was used, and maintained at a temperature of 30° C.
 As mobile phase A, a 0.05% trifluoroacetic acid aqueous solution was used.
 As mobile phase B, a 0.05% trifluoroacetic acid acetonitrile solution was used.

As sample solutions, samples were diluted with an acetonitrile/water mixture (9:1) so that the concentration of enzalutamide was 240 µg/mL.

The amounts of related substances were measured using an ultraviolet absorption spectrophotometer (wavelength: 260 nm), in accordance with the gradient program shown in Table 17 below, and by adjusting the flow rate to 1 mL/min The percentage of the peak area of the maximum related substance was calculated, as a percentage with respect to the total peak area of enzalutamide and its related substances.

TABLE 17

| Time after injection (min.) | Mobile phase A (%) | Mobile phase B (%) |
| --- | --- | --- |
| 0 → 30 | 90 → 10 | 10 → 90 |
| 30 → 31 | 10 → 90 | 90 → 10 |
| 31 → 40 | 90 | 10 |

The results of Experimental Example 10 are shown in Table 18.

TABLE 18

|  | Ex. 9 | Ex. 10 |
| --- | --- | --- |
| Amount of maximum related substance | 0.20% | 0.24% |

Example 11

In a mortar, 1200 mg of the pharmaceutical composition (solid dispersion) of Example 9, 1446 mg of mannitol (PEARLITOL 200SD), 720 mg of potassium chloride, 180 mg of crospovidone (Kollidon CL), 36 mg of light anhydrous silicic acid (Silysia 320TP), and 18 mg of magnesium stearate were prepared, and mixed using a pestle. The resulting mixed powder was tableted using a single punch tableting machine to obtain a pharmaceutical composition (tablets, 600 mg per tablet) of Example 11.

Example 12

In a mortar, 1200 mg of the pharmaceutical composition of Example 9, 1446 mg of mannitol (PEARLITOL 200SD), 720 mg of sodium chloride, 180 mg of crospovidone (Kollidon CL), 36 mg of light anhydrous silicic acid (Silysia 320TP), and 18 mg of magnesium stearate were prepared, and mixed using a pestle. The resulting mixed powder was tableted using a single punch tableting machine to obtain a pharmaceutical composition (tablets, 600 mg per tablet) of Example 12.

Example 13

In a mortar, 1200 mg of the pharmaceutical composition of Example 9, 1446 mg of mannitol (PEARLITOL 200SD), 720 mg of magnesium chloride hexahydrate, 180 mg of crospovidone (Kollidon CL), 36 mg of light anhydrous silicic acid (Silysia 320TP), and 18 mg of magnesium stearate were prepared, and mixed using a pestle. The resulting mixed powder was tableted using a single punch tableting machine to obtain a pharmaceutical composition (tablets, 600 mg per tablet) of Example 13.

TABLE 19

|  | Ex. 11 | Ex. 12 | Ex. 13 |
|---|---|---|---|
| Ex. 9 | 200 | 200 | 200 |
| Mannitol | 241 | 241 | 241 |
| Potassium chloride | 120 | — | — |
| Sodium chloride | — | 120 | — |
| Magnesium chloride hexahydrate | — | — | 120 |
| Crospovidone | 30 | 30 | 30 |
| Light anhydrous silicic acid | 6 | 6 | 6 |
| Magnesium stearate | 3 | 3 | 3 |
| Total | 600 | 600 | 600 |

(Unit: mg)

<<Experimental Example 11>> Dissolution Test

A dissolution test of the pharmaceutical compositions (tablets containing 40 mg equivalent of enzalutamide) prepared in Examples 11 to 13 was carried out. The dissolution test was carried out using water (test fluid volume: 500 mL, fluid temperature: 37° C.) as a dissolution test fluid in accordance with a Dissolution Test, a paddle method of the Japanese Pharmacopoeia at a paddle rotation speed of 50 rpm. The ultraviolet absorbance of enzalutamide was measured at 260 nm. The dissolution rate was calculated when an absorbance of 0.3158 in a 1-mm cell was regarded as 100%.

The dissolution rates after 10 minutes from the beginning of the dissolution test ($D_{10min}$) are shown in Table 20. A high dissolution rate of 60% or higher was observed in Example 13, using magnesium chloride hexahydrate. Further, extremely high dissolution rates of 80% or higher were obtained in Example 11 using potassium chloride and Example 12 using sodium chloride.

TABLE 20

|  | Ex. 11 | Ex. 12 | Ex. 13 |
|---|---|---|---|
| $D_{10\ min}$ (%) | 100.1 | 92.5 | 72.7 |

<<Experimental Example 12>> Oral Absorption Test in Dog

The pharmaceutical composition (tablets containing 160 mg equivalent of enzalutamide (four tablets)) prepared in Example 11, and XTANDI (registered trademark) Capsules were orally administered to four male beagle dogs separately under fasting conditions. The test was carried out under the same test conditions as those in Experimental Example 6.

The maximum plasma concentration of an unchanged form (Cmax), the area under the plasma concentration time curve of an unchanged form from 0 to 24 hours (AUC), and the time to reach the maximum plasma concentration of an unchanged form (Tmax) of the pharmaceutical composition of Example 11, and the XTANDI (registered trademark) Capsules, and the ratios thereof to the values of the XTANDI Capsules (GMR) are shown in Table 21. In Example 11, both Cmax and AUC were higher than those of the XTANDI (registered trademark) Capsules, and a high absorbability was obtained. Further, in Example 11, Tmax was shorter than that of the XTANDI (registered trademark) Capsules, and a rapid absorbability was observed.

TABLE 21

|  |  | XTANDI capsules | Ex. 11 |
|---|---|---|---|
| Cmax | µg/mL | 16.0 ± 6.6 | 15.9 ± 3.1 |
|  | GMR | — | 1.05 |
| AUG | µg/mL · h | 266.9 ± 101.6 | 274.0 ± 70.1 |
|  | GMR | — | 1.06 |
| Tmax | h | 8.00 ± 2.83 | 5.75 ± 4.92 |

Example 14

In a mortar, 4000 mg of the pharmaceutical composition (solid dispersion) of Example 10, 4820 mg of mannitol (PEARLITOL 200SD), 2400 mg of potassium chloride, 600 mg of crospovidone (Kollidon CL), 120 mg of light anhydrous silicic acid (Silysia 320TP), and 60 mg of magnesium stearate were prepared, and mixed using a pestle. The resulting mixed powder was tableted using a single punch tableting machine to obtain a pharmaceutical composition (tablets, 600 mg per tablet) of Example 14.

Example 15

In a mortar, 2000 mg of the pharmaceutical composition (solid dispersion) of Example 10, 2410 mg of mannitol (PEARLITOL 200SD), 1200 mg of sodium chloride, 300 mg of crospovidone (Kollidon CL), 60 mg of light anhydrous silicic acid (Silysia 320TP), and 30 mg of magnesium stearate were prepared, and mixed using a pestle. The resulting mixed powder was tableted using a single punch tableting machine to obtain a pharmaceutical composition (tablets, 600 mg per tablet) of Example 15.

Example 16

In a mortar, 2000 mg of the pharmaceutical composition (solid dispersion) of Example 10, 2410 mg of mannitol (PEARLITOL 200SD), 1200 mg of potassium dihydrogen phosphate, 300 mg of crospovidone (Kollidon CL), 60 mg of light anhydrous silicic acid (Silysia 320TP), and 30 mg of magnesium stearate were prepared, and mixed using a pestle. The resulting mixed powder was tableted using a single punch tableting machine to obtain a pharmaceutical composition (tablets, 600 mg per tablet) of Example 16.

TABLE 22

|  | Ex. 14 | Ex. 15 | Ex. 16 |
|---|---|---|---|
| Ex. 10 | 200 | 200 | 200 |
| Mannitol | 241 | 241 | 241 |
| Potassium chloride | 120 | — | — |
| Sodium chloride | — | 120 | — |
| Potassium dihydrogen phosphate | — | — | 120 |
| Crospovidone | 30 | 30 | 30 |
| Light anhydrous silicic acid | 6 | 6 | 6 |
| Magnesium stearate | 3 | 3 | 3 |
| Total | 600 | 600 | 600 |

(Unit: mg)

<<Experimental Example 13>> Dissolution Test

A dissolution test of the pharmaceutical compositions (tablets containing 40 mg equivalent of enzalutamide) prepared in Examples 14 to 16 was carried out. The dissolution test was carried out using water (test fluid volume: 500 mL, fluid temperature: 37° C.) as a dissolution test fluid in accordance with a Dissolution Test, a paddle method of the Japanese Pharmacopoeia at a paddle rotation speed of 50 rpm. The ultraviolet absorbance of enzalutamide was measured at 260 nm. The dissolution rate was calculated when an absorbance of 0.3158 in a 1-mm cell was regarded as 100%.

The dissolution rates after 10 minutes from the beginning of the dissolution test ($D_{10min}$) are shown in Table 23. Extremely high dissolution rates of 80% or higher were obtained in any of the Examples.

TABLE 23

|  | Ex. 14 | Ex. 15 | Ex. 16 |
|---|---|---|---|
| $D_{10\,min}$ (%) | 103.5 | 86.3 | 85.5 |

<<Experimental Example 14>> Oral Absorption Test in Dog

The pharmaceutical composition (tablets containing 160 mg equivalent of enzalutamide (four tablets)) prepared in Example 14, and XTANDI (registered trademark) Capsules were orally administered to three male beagle dogs separately under fasting conditions. The test was carried out under the same test conditions as those in Experimental Example 6.

The maximum plasma concentration of an unchanged form (Cmax), the area under the plasma concentration time curve of an unchanged form from 0 to 24 hours (AUC), and the time to reach the maximum plasma concentration of an unchanged form (Tmax) of the pharmaceutical composition (tablets) of Example 14, and the XTANDI (registered trademark) Capsules, and the ratios thereof to the values of the XTANDI Capsules (GMR) are shown in Table 24. In Example 14, both Cmax and AUC showed high values in comparison with those of the XTANDI (registered trademark) Capsules, and a high absorbability was obtained. Further, in the pharmaceutical composition (tablets) of Example 14, Tmax was shorter than that of the XTANDI (registered trademark) Capsules, and a rapid absorbability was observed.

TABLE 24

|  |  | XTANDI capsules | Ex. 14 |
|---|---|---|---|
| Cmax | μg/mL | 18.6 ± 2.6 | 21.5 ± 4.6 |
|  | GMR | — | 1.15 |
| AUG | μg/mL · h | 326.2 ± 48.9 | 375.8 ± 73.0 |
|  | GMR | — | 1.15 |
| Tmax | h | 7.00 ± 1.73 | 5.50 ± 4.33 |

Example 17

In a mortar, 1200 mg of the pharmaceutical composition of Example 9, 1266 mg of mannitol (PEARLITOL 200SD), 720 mg of potassium chloride, 360 mg of crospovidone (Kollidon CL), 36 mg of light anhydrous silicic acid (Silysia 320TP), and 18 mg of magnesium stearate were prepared, and mixed using a pestle. The resulting mixed powder was tableted using a single punch tableting machine to obtain a pharmaceutical composition (tablets, 600 mg per tablet) of Example 17.

Example 18

In a mortar, 1200 mg of the pharmaceutical composition of Example 9, 1266 mg of mannitol (PEARLITOL 200SD), 720 mg of potassium chloride, 360 mg of low substituted hydroxypropylcellulose (L-HPC, LH-21), 36 mg of light anhydrous silicic acid (Silysia 320TP), and 18 mg of magnesium stearate were prepared, and mixed using a pestle. The resulting mixed powder was tableted using a single punch tableting machine to obtain a pharmaceutical composition (tablets, 600 mg per tablet) of Example 18.

TABLE 25

|  | Ex. 17 | Ex. 18 |
|---|---|---|
| Ex. 9 | 200 | 200 |
| Mannitol | 211 | 211 |
| Potassium chloride | 120 | 120 |
| Crospovidone | 60 | — |
| Low substituted hydroxypropylcellulose | — | 60 |
| Light anhydrous silicic acid | 6 | 6 |
| Magnesium stearate | 3 | 3 |
| Total | 600 | 600 |

(Unit: mg)

<<Experimental Example 15>> Dissolution Test

A dissolution test of the pharmaceutical compositions (tablets containing 40 mg equivalent of enzalutamide) prepared in Examples 17 and 18 was carried out. The dissolution test was carried out using water (test fluid volume: 500 mL, fluid temperature: 37° C.) as a dissolution test fluid in accordance with a Dissolution Test, a paddle method of the Japanese Pharmacopoeia at a paddle rotation speed of 50 rpm. The ultraviolet absorbance of enzalutamide was measured at 260 nm. The dissolution rate was calculated when an absorbance of 0.3158 in a 1-mm cell was regarded as 100%.

The dissolution rates after 10 minutes from the beginning of the dissolution test ($D_{10min}$) are shown in Table 26. Extremely high dissolution rates of 80% or higher were observed in the pharmaceutical compositions (tablets) of Example 17 using crospovidone and Example 18 using low substituted hydroxypropylcellulose.

TABLE 26

|  | Ex. 17 | Ex. 18 |
|---|---|---|
| $D_{10\,min}$ (%) | 91.4 | 90.6 |

Example 19

In 40 mL of water, 3 g of "A1" was stirred until dissolved. To a mixed solution prepared by further adding 160 mL of methanol to the "A1" solution, 1 g of enzalutamide was added and stirred until dissolved to prepare a spray solution. The spray solution was spray-dried with a spray dryer (Niro SD-Micro™ Spray Dryer, GEA) to obtain a pharmaceutical composition (a solid dispersion) of Example 19.

<<Experimental Example 16>> Dissolution Test

A dissolution test of the pharmaceutical compositions (solid dispersions) prepared in Examples 5 to 7 and 19

(containing 80 mg equivalent of enzalutamide) was carried out. The formulation of each pharmaceutical composition is shown in Table 27. Powder mixed with the same amount of mannitol (PEARLITOL 200SD) as that of each pharmaceutical composition (solid dispersion) was used for the test. The dissolution test was carried out using water (test fluid volume: 500 mL, fluid temperature: 37° C.) as a dissolution test fluid in accordance with a Dissolution Test, a paddle method of the Japanese Pharmacopoeia at a paddle rotation speed of 50 rpm (250 rpm for 0 to 3 minutes from the beginning of the test, and 200 rpm for 3 to 5 minutes). The ultraviolet absorbance of enzalutamide was measured at 260 nm. The dissolution rate was calculated when an absorbance of 0.6316 in a 1-mm cell was regarded as 100%.

TABLE 27

|  | Ex. 5 | Ex. 6 | Ex. 7 | Ex. 19 |
| --- | --- | --- | --- | --- |
| Enzalutamide | 80 | 80 | 80 | 80 |
| B5 | 240 | — | — | — |
| B2 | — | 240 | — | — |
| B3 | — | — | 240 | — |
| A1 | — | — | — | 240 |

(Unit: mg)

The dissolution rates after 10 minutes from the beginning of the dissolution test ($D_{10min}$) are shown in Table 28. A high dissolution rate of 100% or higher were obtained in the pharmaceutical composition (solid dispersion) of Example 19 using polyvinyl alcohol having a saponification degree of 66 mol %. In the pharmaceutical composition (solid dispersion) of Examples 5 to 7 using polyvinyl alcohol having a saponification degree of 88 mol % or more, even the pharmaceutical composition of Example 7 showed a dissolved concentration of 15.2 μg/mL (=80 mg×9.5%/500 mL), and an improvement effect of 7 times or more in the dissolved concentration was observed, with respect to the solubility of enzalutamide in water.

TABLE 28

|  | Ex. 5 | Ex. 6 | Ex. 7 | Ex. 19 |
| --- | --- | --- | --- | --- |
| $D_{10\,min}$ (%) | 14.1 | 26.0 | 9.5 | 112.6 |

INDUSTRIAL APPLICABILITY

According to the present invention, a pharmaceutical composition for oral administration, wherein the solubility and/or dissolution properties of enzalutamide are improved, supersaturation is maintained, and the oral absorbability of enzalutamide is improved, can be provided.

Although the present invention has been described with reference to specific embodiments, various changes and modifications obvious to those skilled in the art are possible without departing from the scope of the appended claims.

The invention claimed is:

1. A pharmaceutical composition for oral administration, comprising enzalutamide and polyvinyl alcohol, wherein the polyvinyl alcohol has a saponification degree of 55 mol% or more and less than 85 mol% and a polymerization degree of 100 to 500.

2. The pharmaceutical composition for oral administration according to claim 1, comprising a solid dispersion comprising the enzalutamide and the polyvinyl alcohol.

3. The pharmaceutical composition for oral administration according to claim 1, further comprising a substance having a functional group capable of functioning as a hydrogen bond acceptor.

4. The pharmaceutical composition for oral administration according to claim 3, wherein the substance having a functional group capable of functioning as a hydrogen bond acceptor is polyvinyl pyrrolidone and/or copolyvidone.

5. The pharmaceutical composition for oral administration according to claim 1, further comprising a disintegrant or a co-disintegrant.

6. The pharmaceutical composition for oral administration according to claim 5, wherein the composition comprises the co-disintegrant and wherein the co-disintegrant is a compound or two or more compounds selected from the group consisting of potassium chloride, sodium chloride, magnesium chloride, and potassium dihydrogen phosphate.

7. The pharmaceutical composition for oral administration according to claim 6, wherein the co-disintegrant is potassium chloride.

8. The pharmaceutical composition for oral administration according to claim 5, wherein the composition comprises the disintegrant and wherein the disintegrant is a compound or two or more compounds selected from the group consisting of crospovidone and low substituted hydroxypropylcellulose.

9. The pharmaceutical composition for oral administration according to claim 5, wherein the composition comprises the disintegrant and wherein the disintegrant is crospovidone.

10. The pharmaceutical composition for oral administration according to claim 1, wherein the pharmaceutical composition is a tablet.

11. The pharmaceutical composition according to claim 1, wherein enzalutamide is amorphous.

12. A method of producing a pharmaceutical composition for oral administration comprising enzalutamide and polyvinyl alcohol, comprising a step of preparing a solid dispersion comprising the enzalutamide and the polyvinyl alcohol, wherein the polyvinyl alcohol has a saponification degree of 55 mol% or more and less than 85 mol% and a polymerization degree of 100 to 500.

13. The method of producing a pharmaceutical composition for oral administration according to claim 12, wherein the solid dispersion is prepared by a hot melt extrusion method.

14. The method of producing a pharmaceutical composition for oral administration according to claim 12, wherein the solid dispersion is prepared by a solvent method.

15. The pharmaceutical composition of claim 1, wherein the polyvinyl alcohol has a saponification degree of 63 mol% or more and less than 82 mol%.

16. The pharmaceutical composition of claim 1, wherein the polyvinyl alcohol has a saponification degree of 66 mol% or more and less than 80 mol%.

17. A pharmaceutical composition for oral administration comprising enzalutamide and polyvinyl alcohol, prepared by the method of claim 12.

* * * * *